(12) United States Patent
Seck (10) Patent No.: US 8,900,518 B2
(45) Date of Patent: Dec. 2, 2014

(54) HEALTHCARE CUM OPTIMAL ILLUMINATION DEVICE

(76) Inventor: Hong Chee Seck, Singapore (SG)

( * ) Notice: Subject to any disclaimer, the term of this patent is extended or adjusted under 35 U.S.C. 154(b) by 383 days.

(21) Appl. No.: 13/547,044

(22) Filed: Jul. 12, 2012

(65) Prior Publication Data

US 2012/0275960 A1 Nov. 1, 2012

Related U.S. Application Data (63) Continuation-in-part of application No. PCT/SG2010/000167, filed on Apr. 26, 2010.

(51) Int. Cl.
*A61L 9/20* (2006.01)
*A62B 15/00* (2006.01)
*F24F 3/056* (2006.01)
*F24F 3/16* (2006.01)

(52) U.S. Cl.
CPC ............... *A62B 15/00* (2013.01); *F24F 3/056* (2013.01); *A61L 9/205* (2013.01); *Y02C 10/08* (2013.01); *F24F 2003/1625* (2013.01); *F24F 2003/1667* (2013.01); *F24F 2003/1682* (2013.01); *A61L 2209/12* (2013.01); *A61L 2209/14* (2013.01)
USPC .......................................... 422/121; 422/120

(58) Field of Classification Search
USPC .......................................... 422/120, 121, 292
See application file for complete search history.

(56) References Cited

U.S. PATENT DOCUMENTS

| 4,926,293 | A | 5/1990 | Saba |
| 5,330,722 | A | 7/1994 | Pick et al. |
| 6,174,340 | B1 | 1/2001 | Hodge |
| 6,666,912 | B1 | 12/2003 | Yan |
| 2009/0122516 | A1 | 5/2009 | Yang |

FOREIGN PATENT DOCUMENTS

| CN | 2864975 | 1/2007 |
| CN | 201145164 Y | 11/2008 |
| JP | 9294817 | 11/1997 |
| NL | 8800812 | 10/1989 |

OTHER PUBLICATIONS

International Search Report of PCT/SG2010/000167.

*Primary Examiner* — Sean E Conley (57) ABSTRACT

This invention provides a healthcare cum optimal illumination device. The inventive device includes at least one frame, at least one light source, and at least one layer of treated filter cover. The light source is disposed in the frame. The light source emits infrared radiation, visible light radiation, and ultraviolet radiation. The visible radiation is used for illumination, and the invisible infrared and ultraviolet radiation is harnessed to improve indoor air quality. The layer of the filter cover is treated with substances of air cleaning properties and encloses the frame. The treated filter cover has at least one opening where air in the frame heated by the infrared radiation flows out from the device and cooler ambient air surrounding the device is drawn through the filter cover into the frame replacing the heated air that has flown out of the device to form air circulation and to perform air purification.

12 Claims, 8 Drawing Sheets

HEALTHCARE CUM OPTIMAL ILLUMINATION DEVICE

CROSS-REFERENCE TO RELATED APPLICATION

This present application is a Continuation-in-part Application of PCT application No. PCT/SG2010/000167 filed on Apr. 26, 2010; the contents of which are hereby incorporated by reference.

BACKGROUND OF THE INVENTION

1. Field of the Invention

This invention relates to an illumination device and, more particularly, to an air purifying healthcare cum optimal illumination device with optimal energy utilization.

2. Description of the Related Art

Electric lamps are mainly used for illumination and decorating purposes since Thomas Edison invented the first incandescent bulb in 1879. Until now, other potentials of the lamps are not fully utilized.

The incandescent lamp is energy inefficient converting only 4-6% of electricity into illumination. The energy saving fluorescent lamp is much more energy efficient converting about 20% of electricity into visible light radiation and the remainder into invisible and unutilized infrared radiation and ultraviolet radiation.

There exist already many air purifiers, fans and light bulbs with air purifying property in the market.

There are prior art patents that use fabric filter treated with photocatalytic materials together with UV radiation and fan positioned within enclosed casing to purify air. U.S. Pat. Nos. 6,666,912 and 5,330,722 disclose stand-alone air cleaning apparatus. But they are not fabric lamps for illumination functions as well.

Prior art patents have also considered incorporation of air purifying properties into fluorescent bulbs. They coated the glass bulbs with photocatalytic materials but without the use of partially enclosed fabric lampshade as filter to capture the air pollutants and without the air circulation functions.

Prior art patents such as CN2864975 have disclosed the use of ultraviolet light from an illumination coating of rare earth phosphor whose wavelength is between 280-400 nm, which is capable of transforming 7-deoxidation ergot cholesterol in the skin into vitamin D[3] or D[2].

Other prior art patents such as JP9294817 has disclosed the features of air purification through ionization and use of biochemical rays and ultraviolet rays to refresh and promote the health of the user.

BRIEF SUMMARY OF THE INVENTION

According to the above, this invention is to provide a healthcare cum optimal illumination device. The inventor has creatively integrated three basic functions of non-glaring illumination, air circulation, and elimination of air borne virus, bacteria, and other microbes and removal of odors, volatile organic compounds (VOC), and other airborne pollutants into a useful, stand-alone, and innovative multi-function healthcare illumination device working at atmospheric pressure and ambient temperature. Such an inventive device which is efficient in terms of using the entire range of electromagnetic radiation from any light source and promotes the physical and mental health and social well being of the people in its surrounding is new and unique.

The healthcare cum optimal illumination device includes at least one frame, at least one light source, and at least one layer of filter cover. The light source is disposed in a cavity of the frame, and the light source emits infrared radiation, visible light radiation, and ultraviolet radiation. The visible radiation is used for illumination, and the invisible infrared radiation and the ultraviolet radiation are harnessed to improve indoor air quality. The at least one layer of the filter cover is treated with substances of air cleaning properties and encloses the frame. The treated filter cover is with at least one opening where air in the frame heated by the infrared radiation flows out readily from the device and cooler ambient air surrounding the device is drawn through the treated filter cover into the cavity of the frame replacing the heated air that has flown out of the device to form air circulation by convection means and to perform air purification.

In one embodiment of the invention, the filter cover may have one layer coated with anti-microbial agents, one layer treated with zinc oxide, copper oxide, or calcium hydroxide, one layer coated with activated carbon or zeolite, one layer coated with doped nano-$TiO_2$, or the combination thereof to capture and remove air pollutants at surfaces of the filter cover.

In one embodiment of the invention, the healthcare cum optimal illumination device may further include a chassis disposed at the top of the frame, with the at least one light source disposed at the chassis.

In one embodiment of the invention, the healthcare cum optimal illumination device may further include an ionizer disposed at the chassis to improve indoor air quality outside the device.

In one embodiment of the invention, the healthcare cum optimal illumination device may further include at least one container containing antimicrobial and fragrant essential oil disposed in the cavity of the frame to disinfect and refresh indoor air outside the healthcare cum optimal illumination device.

In one embodiment of the invention, the healthcare cum optimal illumination device may further include a base plate disposed between two frames so that the base plate enables the device to be connectable, scalable, flexible facilitating adds-on and multi-functions.

In one embodiment of the invention, the healthcare cum optimal illumination device may further include at least one electric fan disposed at the base plate to enhance air circulation and air filtration by mechanical means.

In one embodiment of the invention, the healthcare cum optimal illumination device may further include an audio system disposed at the base plate enabling the installation of software for music, singing, dancing, exercise, meditation, reading, inducing stress relief, relaxation, rest, and sleep that contribute to the well-being of users.

In one embodiment of the invention, the healthcare cum optimal illumination device may further include a safety mesh disposed at the top of the frame.

In one embodiment of the invention, the frame may be in a taper shape or a half shape to be capable of being stacked on each other and to be connected for scalability and reduction of space, carbon footprint and costs.

In one embodiment of the invention, the healthcare cum optimal illumination device may further include a photocatalytic air cleaner (PAC). The PAC includes an ultraviolet light source, a base plate, an electric fan, and two or more layers of the treated filter cover. The ultraviolet light source is disposed in the cavity of the frame, the base plate is disposed at the top of the frame, and the inner layer of the filter cover is treated with doped nano-TiO$_2$ and encloses the frame for capturing and decomposing air pollutants by photocatalysis at surfaces of the filter cover.

In one embodiment of the invention, the light source may include different electric light sources capable of emitting light in different colors and brightness.

To sum up, the inventive device can be modular and non-modular in combination so that standard frames of various shapes, sizes, designs, colors, materials can be joined together to form larger size lamps with large number of configurations. With such an approach, the inventive device is connectable, scalable, and flexible and can therefore be designed and made to configurate and accommodate varying room size ranging from a small bedroom to the lobby of a hotel to even the interior of a shopping mall and other large buildings. With such an approach, the inventory requirements of standard frames can be greatly reduced because of standard sizes and common parts.

Further, the shape of each standard frame is either slightly tapered/slanted or in symmetrical half-shaped so that they can be stacked together to minimize space/volume required during storage and transportation and saving in packaging and delivery which will also reduce the carbon footprint and resources required.

In addition, the inventive device not only can be covered with various types of treated filter covers for air cleaning but also for deco-matching and with materials, patterns and colors which can be changed to keep up with festive occasions and moods of the people and also with changing trends in interior design, thereby would not become obsolete.

It is desirable if the inventive device uses the combined features of a selection of devices with proven air cleaning technologies, a selection of treated filter cover with anti-microbial properties and other air cleaning properties, all of which can be preset by the user from the said selection depending on the indoor air qualities to meet not only the physical health conditions of the users and at the same time improve the mental health and social well being of the users through control of lighting of various colors and brightness and with improvement of ambience through music and other audio-visual therapies and also with essential oil which have antimicrobial aromatherapeutic properties. The audio-visual devices will not only create sound and sight conditions to help relaxation, rest and sleep but can also stimulate and facilitate physical movements and social interaction such as dancing, singing, exercising, etc using various hardware and software for various health problems and healthcare solutions.

The innovative integration of these capabilities and technologies for healthy indoor living, which is sustainable and caring, is an open flexi-add-on multi-function system and continuous air flow process powered by convection means and/or mechanical means to improve indoor air quality and to provide visual comfort with energy optimization. This system is called SC Technology or SC Tec in short.

These and other features, aspects, and advantages of the present invention will become better understood with regard to the following description, appended claims, and accompanying drawings.

DETAILED DESCRIPTION OF THE INVENTION

Figure 1:
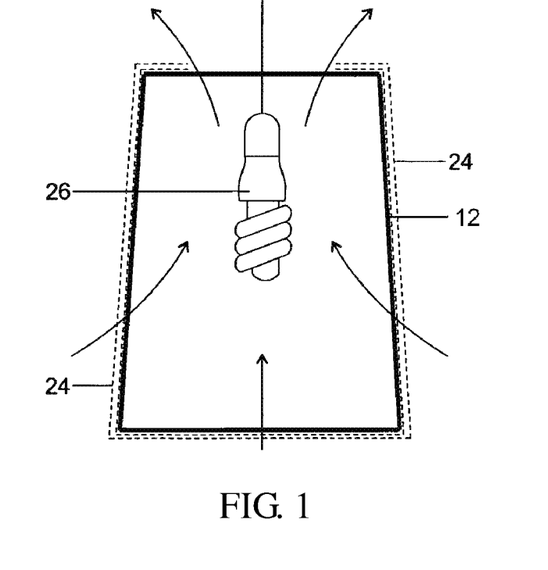
FIG. 1 is a schematic diagram showing a healthcare cum optimal illumination device according to a basic embodiment of this invention.

FIG. 1 is a schematic diagram showing a healthcare cum optimal illumination device according to a basic embodiment of this invention. In FIG. 1, the healthcare cum optimal illumination device includes at least one frame 12, at least one light source 26, and at least one layer of filter cover 24. The light source 26 is disposed in a cavity of the frame 12, and the light source 26 emits infrared radiation, visible light radiation, and ultraviolet radiation. The visible radiation is used for illumination, and the invisible infrared radiation and the ultraviolet radiation are harnessed to improve indoor air quality. The at least one layer of the filter cover 24 is treated with substances of air cleaning properties and encloses the frame 12. The treated filter cover 24 is with at least one opening where air in the frame 12 heated by the infrared radiation flows out readily from the device and cooler ambient air surrounding the device is drawn through the treated filter cover 24 into the cavity of the frame 12 replacing the heated air that has flown out of the device to form air circulation by convection means and to perform air purification.

The frame 12 is shown in bold black lines, and the dashed lines represent the layers of the treated filter cover 24 covering the frame 12. The arrows show the convectional air inflowing through the filter cover 24 and the heated air outflowing through the upper end of the inventive device.

In the embodiment, the shape of the cross section of the frame 12 is circular. However, the invention is not limited thereto. In other embodiments, the cross section of the frame 12 may be oval, square, rectangular, triangular, pentagonal, octagonal, D-shaped, or in other shapes. Further, the frame 12 may be a cylinder, a cone, a cube, a hemisphere, a sphere, an oblong, a cup, a bird cage, or in any other shapes. The shape, size and material of the frame 12 are not limited in the invention. In other words, the frame 12 can be in various shapes, sizes, and materials.

In the embodiment, the cross sectional area of the upper portion of the frame 12 is smaller than that of the lower portion of the frame 12. However, the invention is not limited thereto. In other embodiments, the cross sectional area of the upper portion of the frame 12 can be equal to or be larger than that of the lower portion of the frame 12.

The frame 12 in the embodiment can be standard, connectable, and scalable. Thus, several frames 12 can be combined and connected with each other to form scalable devices of various configurations, shapes, and sizes for more functions and higher efficacy.

In the embodiment, the frame 12 may be in a taper shape or a half shape to be capable of being stacked on each other and to be connected for scalability and reduction of space, carbon footprint, and costs.

In the embodiment, the filter cover 24 may have one layer coated with anti-microbial agents, one layer treated with zinc oxide, copper oxide, or calcium hydroxide, one layer coated with activated carbon or zeolite, one layer coated with doped nano-$TiO_2$, or the combination thereof to capture and remove air pollutants at surfaces of the filter cover. The filter cover 24 not only acts as a lamp shade for aesthetic and anti-glare purposes but also acts as a filter for trapping and holding air borne pollutants. Furthermore, the filter cover 24 acts as a substrate for holding various air cleaning chemicals/substances and as a protective cover.

In detail, a few layers of the filter cover 24 are shown wrapped around the frame 12. The layers of filter cover 24 can be changed to suit the indoor air quality and the health requirements of users. The layers can include: a layer treated with anti-microbial agents to trap and kill microbes physically by stabbing and electrocution; a layer treated with bactericides like ZnO, CuO or $Ca(OH)_2$ to trap and kill bacteria and also to neutralize acidic gases like $CO_2$, $NO_x$, $SO_x$, HCl, etc; a layer treated with activated carbon as sorbent to remove odors and ozone; and a layer having doped nano photocatalytic material to decompose and detoxify the trapped volatile organic compounds (VOC), odors, microbes, spores, danders, and other harmful air pollutants upon radiation with ultraviolet light to innocuous molecules like $H_2O$, $CO_2$, and inorganic salts by redox reactions.

The filter cover 24 can be printed with words and pictures to be used as an advertisement, a notice, a sign, a display screen for motivational and wisdom writings, or a spiritual and inspirational message.

The filter cover 24 in the invention can be washed with water to dispose the undecomposed substances and can be dried to be reused. In the application, the outermost layer of the filter cover 24 can be washed normally almost once a month. The inner layer(s) of the filter cover 24 can be washed normally once every three months depending on the environmental conditions. Therefore, the filter cover 24 can maintain its filtration and disinfecting functions.

In the embodiment, the light source 26 includes different electric light sources capable of emitting light in different colors and brightness. The inventive device can be a floor lamp, a table lamp, a wall lamp, a pendant lamp, or a ceiling lamp of various shapes, sizes, colors, materials, and configurations incorporated with various air cleaning technologies as standard products as well as customized in a flexible and add-on manner catering to the specific requirements for the preservation of health and enhancement of physical, mental and social well-being of various users according to the invention's purpose that coincides with the World Health Organization's definition of health.

Figure 2:
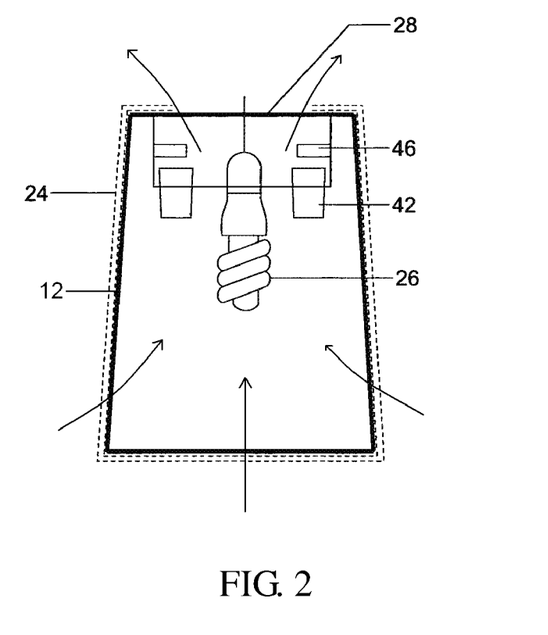
FIG. 2 is a schematic diagram showing the inventive device as a pendant lamp according to one embodiment of the invention.
Figure 2A:
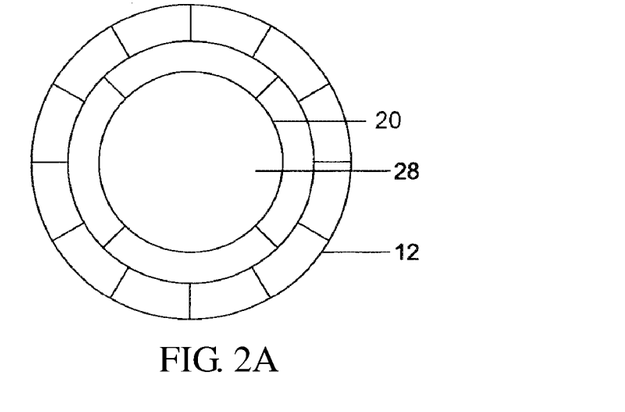
FIG. 2A is a top view showing a frame with a safety mesh of the inventive device according to the embodiment of the invention.
Figure 2B:
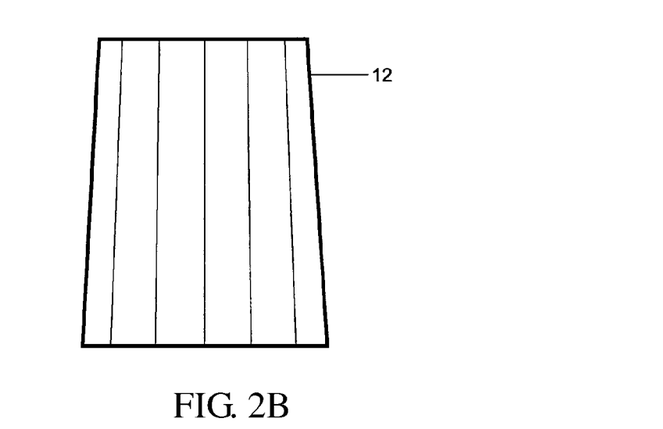
FIG. 2B is a side view showing the frame according to the embodiment of the invention.
Figure 2C:
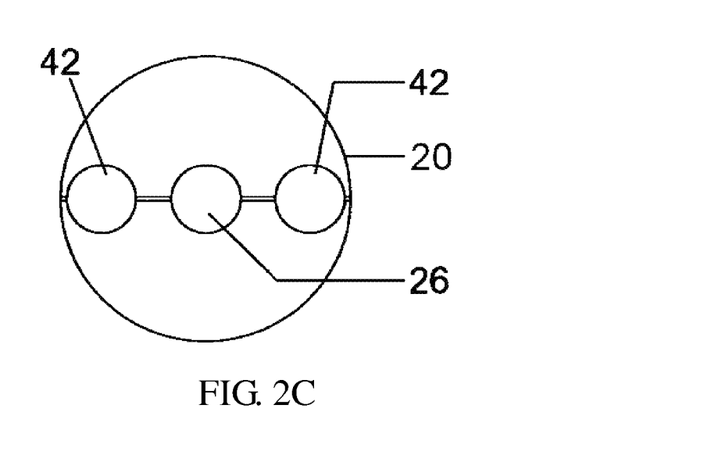
FIG. 2C is a top view showing a chassis with one light source and two essential oil containers of the inventive device according to the embodiment of the invention.

FIG. 2 is a schematic diagram showing the inventive device as a pendant lamp according to one embodiment of the invention. FIG. 2A is a top view showing a frame with a safety mesh of the inventive device according to the embodiment of the invention. FIG. 2B is a side view showing the frame according to the embodiment of the invention. FIG. 2C is a top view showing a chassis with one light source of the inventive device according to the embodiment of the invention. Please refer to FIG. 2 to FIG. 2C together.

In the embodiment, the inventive device further includes a chassis 20 disposed at the top of the frame 12, with the at least one light source 26 disposed at the chassis 20. Different components with different functions can be connected with the device by being disposed at the chassis 20.

In the embodiment, the inventive device further includes an ionizer 46 disposed at the chassis 20 to improve indoor air quality outside the device. In the embodiment, the ionizer 46 can be a plasma ionizer with several negative and positive ion emitters each producing a few millions of negative and positive ions per c.c. per second. The sprays of charged particles or plasma will spread throughout the surroundings by air circulation and Brownian diffusion movement generated by the inventive device to clean the air outside the device. However, the invention is not limited thereto. In other embodiments, the ionizer 46 may be an anion ionizer with at least one negative ion emitter fixed on the chassis 20.

In the embodiment, the inventive device further includes at least one container 42 containing antimicrobial and fragrant essential oil disposed at the chassis 20 to disinfect and refresh indoor air outside the inventive device. In one application, the container 42 can contain perfumed materials or a mixture of different types of essential oil. Since the infrared radiation produces heat, the heat will evaporate the essential oil to allow the essential oil to diffuse throughout the surroundings for air sanitization and for their pleasant fragrance smelling like fresh air in gardens and parks. However, the invention is not limited thereto.

In the embodiment, the inventive device further may include a safety mesh 28 disposed at the top of the frame 12, thus to enhance the safety of the inventive device by restricting access into the device. In the embodiment, the safety mesh 28 is connected to the opening at the top of the frame 12.

Figure 3:
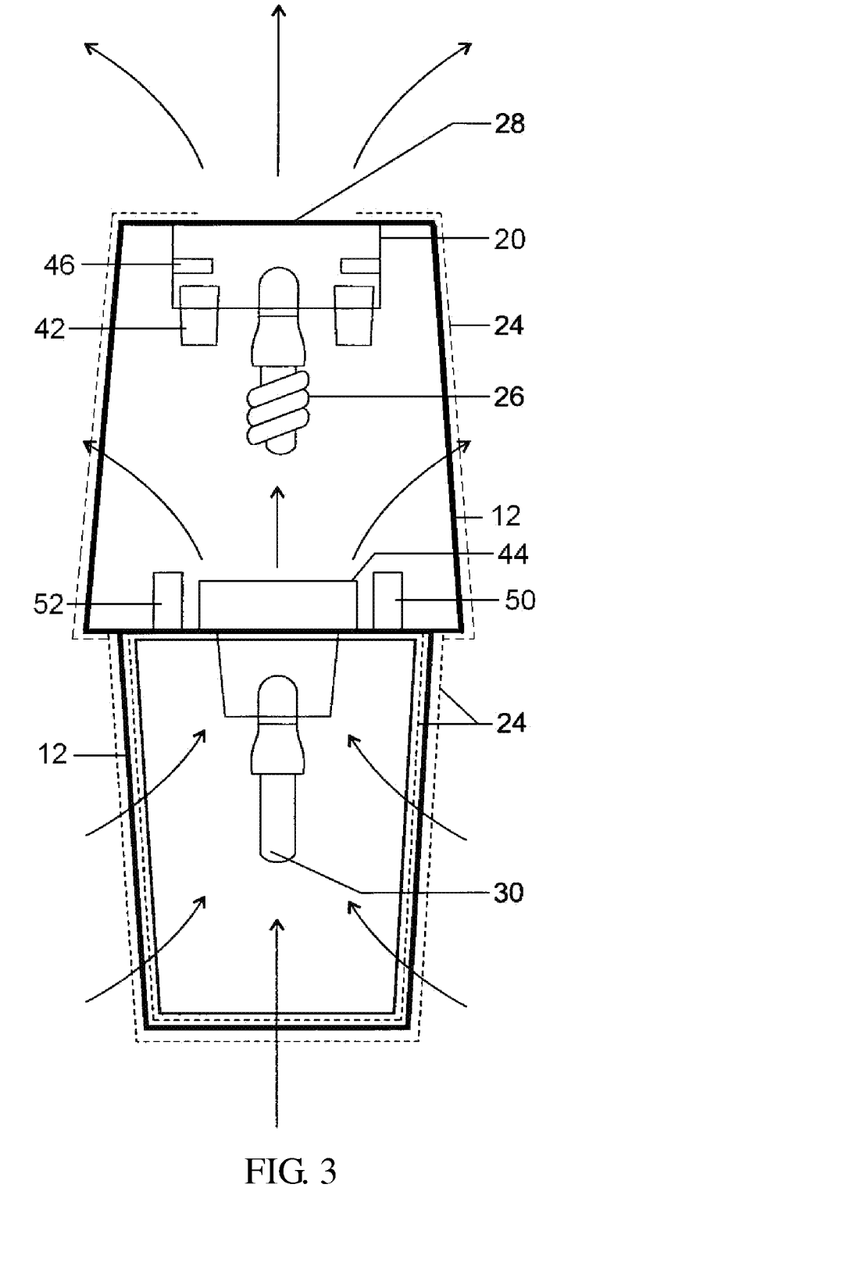
FIG. 3 is a schematic diagram showing the inventive device as a table lamp according to another embodiment of the invention.
Figure 3A:
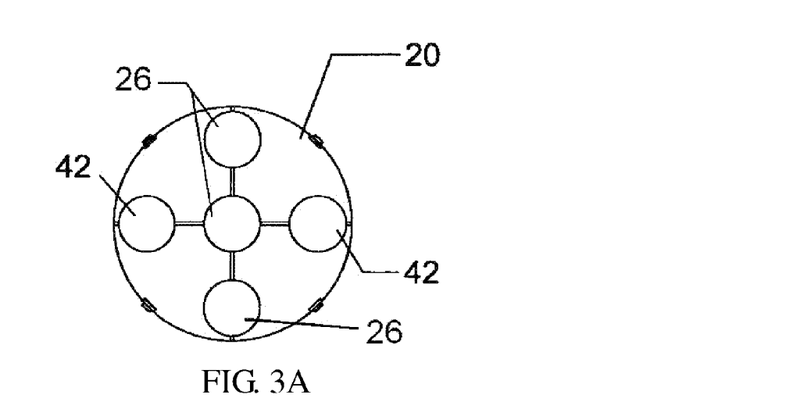
FIG. 3A is a top view showing a chassis with three light sources and two essential oil containers according to the embodiment of the invention.
Figure 3B:
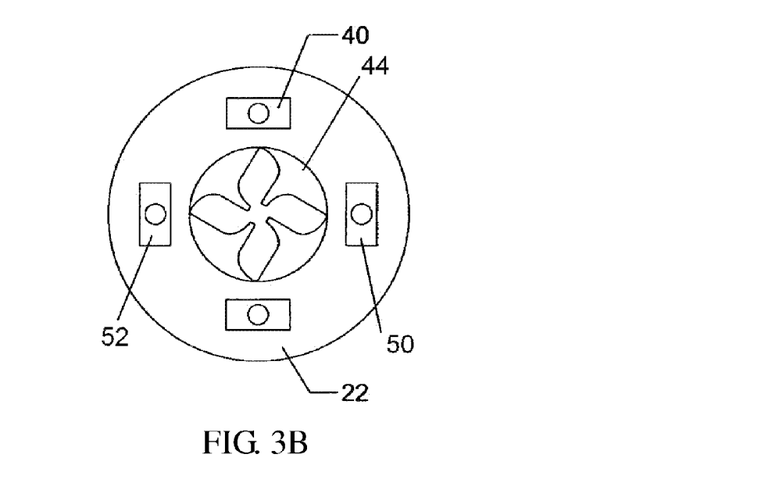
FIG. 3B is a top view showing a base plate according to the embodiment of the invention.
Figure 3C:
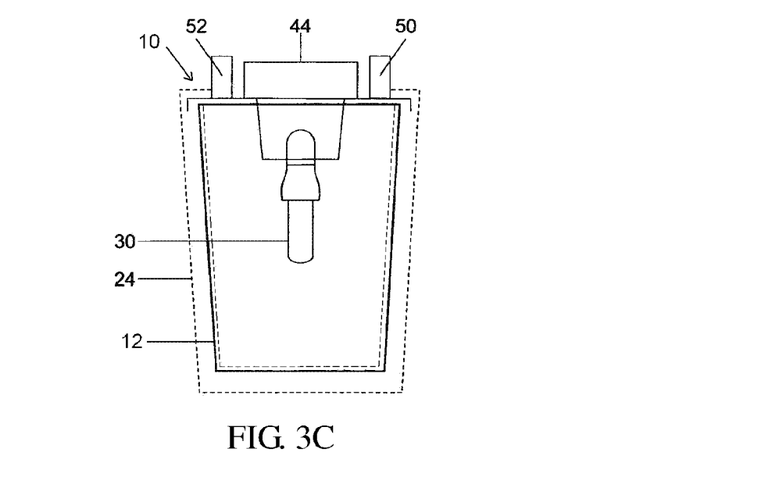
FIG. 3C is a schematic diagram showing a photocatalytic air cleaner (PAC) according to the embodiment of the invention.

FIG. 3 is a schematic diagram showing the inventive device as a table lamp according to another embodiment of the invention. FIG. 3A is a top view showing the chassis with three light sources and two essential oil containers according to the embodiment of the invention. FIG. 3B is a top view showing a base plate according to the embodiment of the invention. FIG. 3C is a schematic diagram showing a photocatalytic air cleaner (PAC) according to the embodiment of the invention. Please refer to FIG. 3 to FIG. 3C together.

In the embodiment, the inventive device further includes a base plate 22 disposed between two frames 12 so that the base plate 22 enables the device to be connectable, scalable, flexible facilitating adds-on and multi-functions.

In the embodiment, the inventive device further includes at least one electric fan 44 disposed at the base plate 22 to enhance air circulation and air filtration by mechanical means. Thus, the efficacy of air filtration is greatly improved. Without the electric fan 44, the air inside and outside the device is circulated only by convection means caused by the infrared radiation. The at least one electric fan 44 can be located at the top, middle, or bottom of the inventive device. If the essential oil is used and the chassis 20 is situated at the top of the inventive device, the fan 44 is preferred to be disposed at the middle of the device. This is because the heat produced by the light source 26 will vaporize the essential oil which will then be lifted upwards and outwards from the inventive device due to the uprising convection current assisted by the electric fan 44 which is located at the middle portion of the inventive device. The removal of heat in the device will also increase the life span of the light bulb.

In the embodiment, the inventive device further includes an audio system 52 disposed at the base plate 22 enabling the installation of software for music, singing, dancing, exercise, meditation, reading, inducing stress relief, relaxation, rest, and sleep that contribute to the health and well-being of users.

In the embodiment, the base plate 22 is provided with several slots 40 to fit an electrostatic unit, a programmable controller 50, the electric fan 44, the audio system 52, and other devices in accordance to user's requirements.

Due to the standardized and modular nature of the inventive device, it is possible for the base plate 22 not to be fitted with any devices and merely be an opening to allow air to flow through. Likewise, it is possible for the chassis 20 not to be fitted with one or more containers of essential oil 42, one or more light sources 26, or one or more ionizers 46.

Therefore, the flexible add-on and modular approach of this inventive device makes it possible for the user to select: the type of components to be fitted into the base plate 22 and the chassis 20; the type, nature, and number of the light source 26; the type and number of the treated filter cover 24 to be used as a lamp shade cover; the type of the essential oil to be used; the type of chemicals to be coated on the filter cover 24; the air filtration efficiency of the filter cover 24 to be used; and all of which can be pre-selected or change according to the health requirements of the users and the indoor environmental conditions.

In the embodiment, the inventive device further includes a PAC 10. The PAC 10 includes an ultraviolet light source 30, the base plate 22, the electric fan 44, and two or more layers of the treated filter cover 24. The ultraviolet light source 30 is disposed in the cavity of the frame 12, the base plate 22 fitted with the electric fan 44 is disposed at the top of the frame 12, and the inner layer of the filter cover 24 is treated with doped nano-$TiO_2$ and encloses the frame 12 for capturing and decomposing air pollutants by photocatalysis at surfaces of the filter cover 24.

In the embodiment, the chassis 20 has three sockets for the light sources 26 and two sockets for the containers 42 containing the essential oil. However, the invention is not limited thereto.

It is possible for each of the lamp shades to be fitted with different layers of the filter cover 24 for various functions so that with one or more layers for each frame 12, strong glare will be diffused to provide soft lighting for visual comfort. Two or more layers of the filter cover 24 increase filtration efficiency because they capture ultra fine and fine particulates including microbes through inertia impaction and diffusion (Brownian movement) in addition to mechanical filtration (sieving).

The air is drawn through the layers of filter cover 24 with anti microbial shield. Various kind of biological (living and dead organisms) and chemical (organic and inorganic substances) air pollutants such as particulates (PM) of various sizes (coarse >2.5 um, fine 2.5-0.1 um and ultra fine <0.1 um), volatile organic compounds (VOC), odors and toxic gases from diverse sources would be captured or adsorbed as indoor air flows through the treated layers. Air cleaning takes place at the filter cover 24 as well as outside the lamp by attaching negative ion and plasma ionizers at the outlet of the inventive device producing several millions of charged particle(s) per c.c. per second and emitting them like shower or spray into the surrounding indoor air containing air pollutants. Air circulation and random Brownian diffusion generated by the inventive device will spread and mix the highly unstable and reactive negative and positive ions with the air pollutants, especially the fine particulates, the ultra fine particulates, and VOC, causing them to be charged, attract oppositely, interact and form larger and heavier particles and clusters. The agglomerated air pollutants cluster will become too large and heavy to remain suspended. Also, germs will be injured or killed when hit repeatedly and continuously by a large number of the highly reactive negative and positive ions. Eventually, they will precipitate from the air by gravitational force. Some falling clusters will be drawn by the gentle circulating airflow powered by the inventive device and be captured by filtration and decomposed by photocatalysis at the filter cover of the lamp.

Indoor air quality (IAQ) is therefore improved through repeated and continuous detoxification/purification by these innovative and integrative applications of various air cleaning technologies outside the device as well as at the treated filter cover 24 of the device.

Since the inventive device is used indoors at home, in offices, schools, and other places, the inventive device would be able to reduce the amounts of virus, bacteria, fungi, spores, pollens, odors, and other pollutants from toxic to non-toxic level in one or two hours, after which it is no longer necessary and cost effective to remove the remaining insignificant amount of air pollutants. In the embodiment, the programmable controller 50 can have various time settings for the operation of the ionizer 46 and the electric fan 44 so that it would switch them off once the setting for each of their time period has been reached. In other embodiments, manual switches or sensors can be used to perform the function.

Based on the basic embodiment of the inventive device using the nano-$TiO_2$ photocatalyst treated filter cover 24 enclosing the frame 12 and the electric fan 44 disposed at the top of the device but without disposing the ionizer 46 and the essential oil 42, two tests were carried out by an independent testing laboratory on an enclosed office room of floor area approximately 9 $m^2$ and room volume of approximately 25 $m^2$. In the test, bacteria and fungi were introduced with common airborne bacteria and fungi culture media for the first five minutes of test duration. Similarly, another test was conducted in the same room, with introduction of nicotine by burning a Marlboro type cigarette for the first five minutes of test duration.

The following results recorded for the first test:

| Cumulative time (mins) | RSP ($mg/m^3$) | MOM (PELTS) ($mg/m^3$) | SIAQG ($mg/m^3$) |
|---|---|---|---|
| 0 | 14.4 | 10 (Nuisance Particulates) | 0.15 (for reference purpose only) |
| 30 | 10.1 | | |
| 60 | 5.4 | | |
| 120 | 1.9 | | |
| 180 | 0.73 | | |
| 240 | 0.62 | | |
| 300 | 0.43 | | |
| 360 | 0.22 | | |
| 420 | 0.08 | | |

Remarks: Respirable Suspended Particulates (RSP) was introduced into the indoor environment with Malboro type cigarettes burning for the first 5 minutes of test duration.

MOM: Ministry of Manpower, Singapore

PELTS: Permissible Exposure Levels of Toxic Substances

SIAQG: Singapore Indoor Air Quality Guidelines
Cumulative time VOC MOM (PELTS) SIAQG (mins) (ppm) (ppm) (ppm)

| Cumulative time (mins) | VOC (ppm) | MOM (PELTS) (ppm) | SIAQG (ppm) |
|---|---|---|---|
| 0 | 987 | Acetone = 750 ppm | 3 (for reference purpose only) |
| 30 | 521 | Trichloroethylene = 50 ppm | |
| 60 | 312 | Isopropyl Alcohol = 400 ppm | |
| 120 | 198 | | |
| 180 | 108 | | |
| 240 | 76 | | |
| 300 | 52 | | |
| 360 | 23 | | |
| 420 | 0 | | |

Remarks: Nicotine was introduced into the indoor environment with Malboro type cigarettes burning for the first 5 minutes of test duration.
The following results recorded for the second test:

| Cumulative time (hrs) | TBC (CFU/m$^3$) | TFC (CFU/m$^3$) | SIAQG (CFU/m$^3$) |
|---|---|---|---|
| 0 | 1110 | 420 | TBC: 500 |
| 1 | 440 | 210 | TFC: 500 |
| 6 | 45 | 30 | |

Remarks: Both Bacteria and Fungi were introduced into the indoor environment with common airborne bacteria and fungi cultures media for the first 5 minutes of test duration.
TBC: Total Bacteria Count TFC: Total Fungi Count

| Cumulative time (hrs) | Nicotine (mg/m$^3$) | OSHA/NIOSH/ACGIA (mg/m$^3$) |
|---|---|---|
| 0 | 0.54 | Acetone = 750 ppm |
| 1 | 0.03 | Trichloroethylene = 50 ppm |
| 6 | 0.01 | Isopropyl Alcohol = 400 ppm |

Remarks: Volatile Organic Compounds (VOC) was introduced into the indoor environment with evaporation of mixed solution comprised of acetone, trichloroethylene and isopropyl alcohol for the first 5 minutes of test duration.

OSHA: Occupational Safety and Health Administration, US

NIOSH: National Institute for Occupational Health & Safety, US

ACGIA: American Conference Of Governmental Industrial Hygieniists, US

The test results showed that after four hours, the inventive device working in a confined space could substantially reduce the amount of bacteria, fungi, odors, and pollutants in a span of four hours using only the basic embodiment of the inventive device with nano-TiO$_2$ coated on the filter cover.

Figure 4:
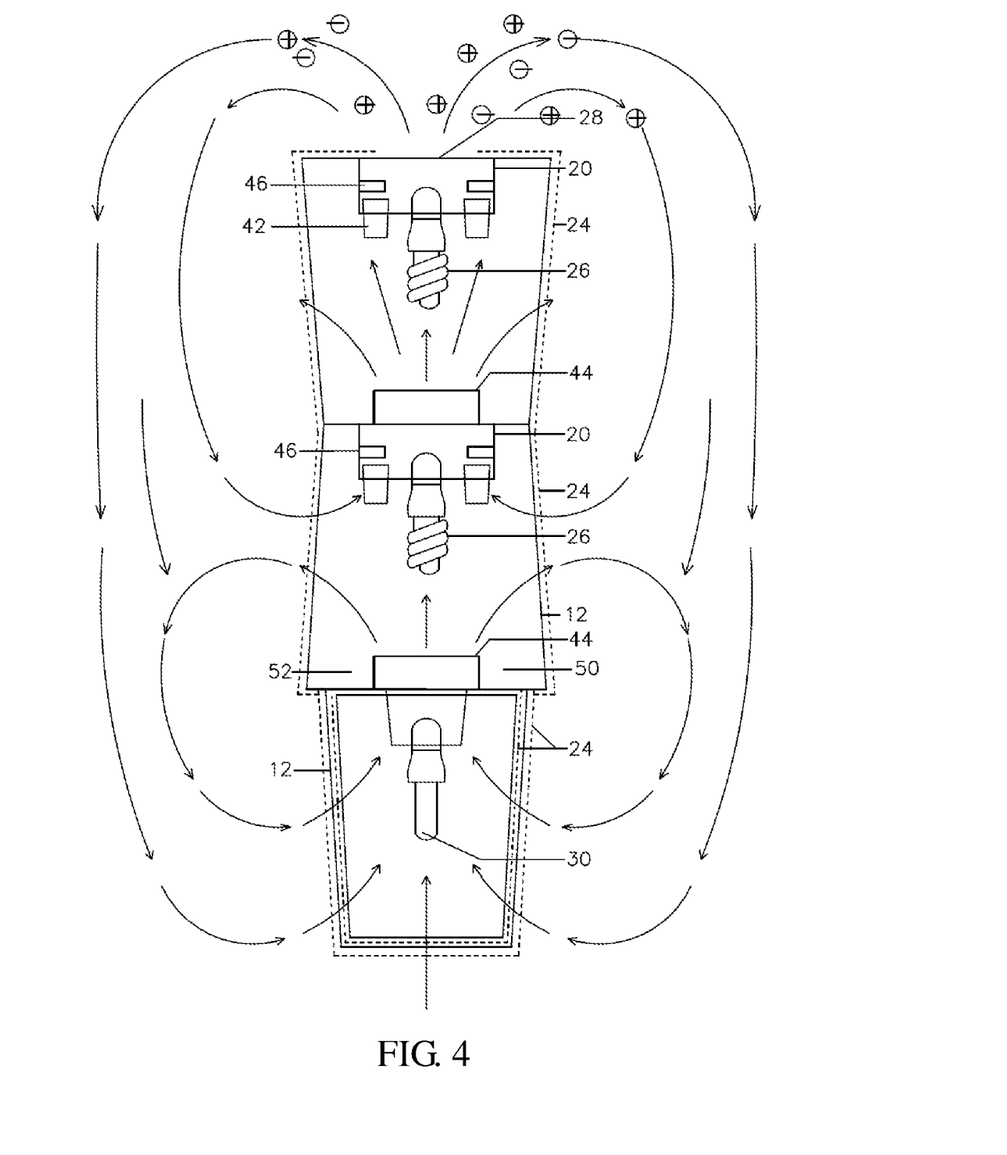
FIG. 4 is a schematic diagram showing the inventive device as a floor lamp according to another embodiment of the invention.

FIG. 4 is a schematic diagram showing the inventive device as a floor lamp according to another embodiment of the invention.

Figures 5A, 5B:
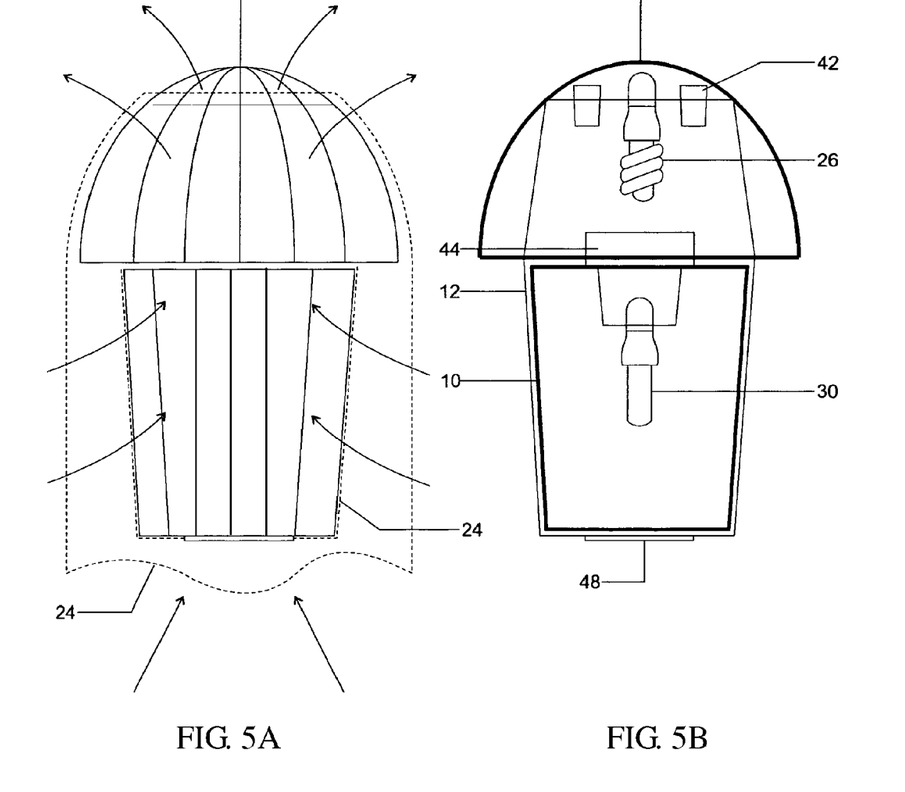
FIG. 5A and FIG. 5B are illustrations of another working embodiment of the invention showing a pendant lamp with LED light source and Treated Deco-Fabric added.

FIG. 5A and FIG. 5B are illustrations of another working embodiment of the invention showing a pendant lamp with LED light source and Treated Deco-Fabric added. This embodiment consists of an upper frame 12 and a lower frame 12 with two light sources 26 and the filter cover 24 as the lamp shade covering the upper frame 12. The lamp shade is semi-hemispherical while the lamp stand is conical in shape. In this variation, the light sources 26 are two fluorescent lamps and a plate of LED 48.

Figures 6A, 6B:
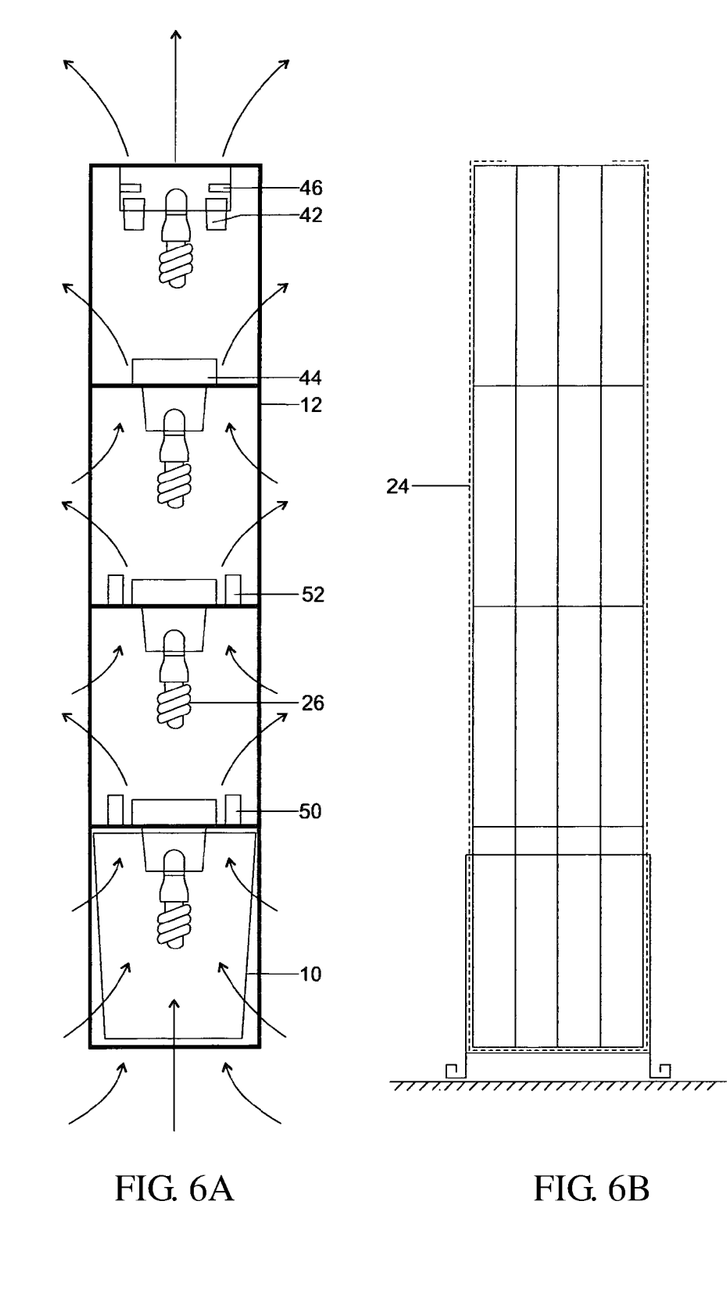
FIG. 6A and FIG. 6B are illustrations of how the modular multi frames floor lamp with very high effectiveness and efficiency can be used to construct a standing inventive device for use in a large interior.

FIG. 6A and FIG. 6B are illustrations of how the modular multi frames floor lamp with very high effectiveness and efficiency can be used to construct a standing inventive device for use in a large interior.

Figure 7A:
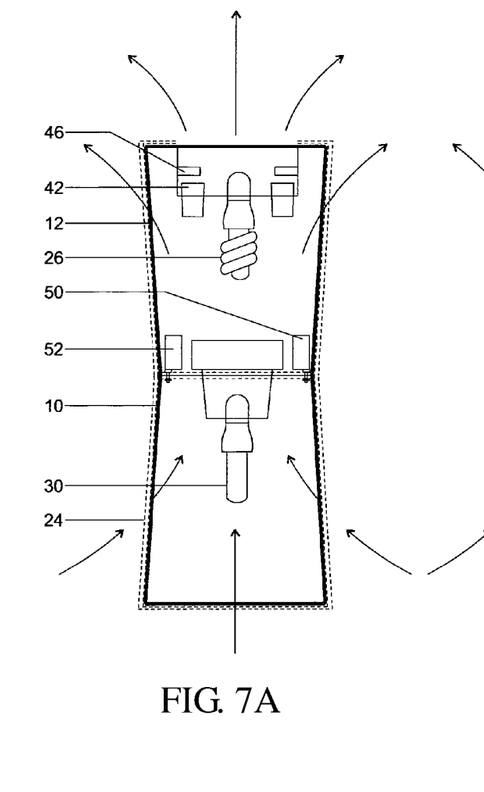
FIG. 7A and FIG. 7B show two variations of frames used to make two different working embodiments of the invention.
Figure 7B:
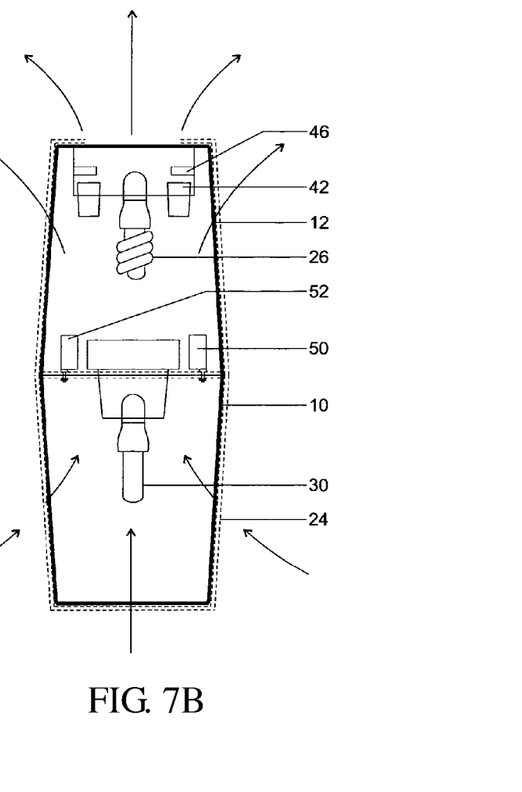

FIG. 7A and FIG. 7B show two variations of frames used to make two different working embodiments of the invention.

Since the filter cover 24 acts like "pull overs" for the lamp shapes, it can be wrapped around the frame 12. For additional layers of the filter cover 24 to be added, the user would have to wrap the additional layer over the inner layers, which are already wrapped around the frame 12. The filter cover 24 is therefore selected by the users to meet the health concerns of users.

For relaxation and to reduce stress, the user may choose an aromatherapeutic essential oil combined with different lights of soft colors and music from the audio system 52 which includes microphones for singing installed in the inventive device.

The above are just a few flexi-add-on combinations to show how the inventive device can promote health. The invention enables the user to use the inventive device in spaces of varying dimensions ranging from very large inventive devices for use in a lobby of an apartment building or a hotel to a lamp in a small room. If the inventive device is used in a large space, it would be fitted with more frames 12, more filter covers 24, more light sources 26, more electric fans 44, more ionizers 46, and also more units of the inventive device to enable it to work effectively in the larger space.

The use of the filter cover 24 and the frame 12 will enhance the safety of the device by restricting access into the partially enclosed lampshade. In the event of accident, the covered lampshade will help to prevent the breaking of the light bulb(s). If the light bulb(s) is/are broken inside the lampshade, the filter cover 24 will hold the harmful broken bulb(s) and provide protection against harms from live electric current and sharp broken glass fused with toxic materials like mercury especially for young children. Additional protection is through the use of the safety mesh 28 on top of the inventive device when necessary. The filter cover 24 wrapped around the PAC 10 also acts to prevent the hands of children from accidentally being placed inside the air purifying lamp.

Although the filter cover 24 is treated, the first and outermost layer of the filter cover 24 can also be used as advertisement signage. The inventive device can have lamp shade covers which are not only treated but can be overprinted with advertisement, notices or motivational messages. Therefore the inventive device can also be used as healthcare light boxes for advertising, learning, and display devices.

The inventive device makes use of the entire spectrum of the visible light, infrared and ultraviolet light emitted by any electric light sources. It not only lights the interior space but improves the indoor air quality by removing air borne pollutants and microbes at the same time. With the removal of air pollutants and heat, the light bulbs will be cleaner, brighter, and cooler and have longer life span.

The innovative integration of these capabilities and technologies for healthy indoor living, which is sustainable and caring, is an open flexi-add-on multi-function system and continuously air flow process powered by convection means and/or mechanical means to improve indoor air quality and to provide visual comfort with energy optimization. This system is called SC Technology or SC Tec in short.

Although the present invention has been described in considerable detail with reference to certain preferred embodiments thereof, the disclosure is not for limiting the scope of the invention. Persons having ordinary skill in the art may make various modifications and changes without departing from the scope and spirit of the invention. Therefore, the scope of the appended claims should not be limited to the description of the preferred embodiments described above.

What is claimed is:

1. A healthcare cum optimal illumination device comprising:
   at least one frame (12);
   at least one light source (26) disposed in a cavity of the frame (12), the light source emitting infrared radiation, visible light radiation, and ultraviolet radiation, the visible radiation used for illumination, the invisible infrared radiation and the ultraviolet radiation harnessed to improve indoor air quality; and
   at least one layer of filter cover (24), treated with substances of air cleaning properties and enclosing the frame (12), the treated filter cover (24) with at least one opening where air in the frame (12) heated by the infrared radiation flows out from the device and cooler ambient air surrounding the device is drawn through the filter cover (24) into the frame (12) replacing the heated air that has flown out of the device to form air circulation by convection means and to perform air purification.

2. The healthcare cum optimal illumination device according to claim 1, wherein the filter cover (24) has one layer coated with anti-microbial agents, one layer treated with zinc oxide, copper oxide, or calcium hydroxide, one layer coated with activated carbon or zeolite, one layer coated with doped nano-$TiO_2$, or the combination thereof to capture and remove air pollutants at surfaces of the filter cover (24).

3. The healthcare cum optimal illumination device according to claim 1, further comprising a chassis (20) disposed at the top of the frame (12), with the at least one light source (26) disposed at the chassis (20).

4. The healthcare cum optimal illumination device according to claim 3, further comprising an ionizer (46) disposed at the chassis (20) to improve indoor air quality outside the device.

5. The healthcare cum optimal illumination device according to claim 1, further comprising at least one container (42) containing antimicrobial and fragrant essential oil disposed in the cavity of the frame (12) to disinfect and refresh indoor air outside the healthcare cum optimal illumination device.

6. The healthcare cum optimal illumination device according to claim 1, further comprising a base plate (22) disposed between two frames (12) so that the base plate (22) enables the device to be connectable, scalable, flexible facilitating adds-on and multi-functions.

7. The healthcare cum optimal illumination device according to claim 6, further comprising at least one electric fan (44) disposed at the base plate (22) to enhance air circulation and air filtration.

8. The healthcare cum optimal illumination device according to claim 6, further comprising an audio system (52) disposed at the base plate (22) enabling the installation of software for music, singing, dancing, exercise, meditation, reading, inducing stress relief, relaxation, rest, and sleep that contribute to the health and well-being of users.

9. The healthcare cum optimal illumination device according to claim 1, further comprising a safety mesh (28) disposed at the top of the frame (12).

10. The healthcare cum optimal illumination device according to claim 1, wherein the frame (12) is in a taper shape or a half shape to be capable of being stacked on each other and to be connected for scalability and reduction of space, carbon footprint, and costs.

11. The healthcare cum optimal illumination device according to claim 1, further comprising a photocatalytic air cleaner (PAC) (10), wherein the PAC (10) includes an ultraviolet light source (30), a base plate (22), an electric fan (44), and two or more layers of the treated filter cover (24), the ultraviolet light source (30) is disposed in the cavity of the frame (12), the base plate (22) fitted with the electric fan (44) is disposed at the top of the frame (12), and the inner layer of the filter cover (24) is treated with doped nano-$TiO_2$ and encloses the frame (12) for capturing and decomposing air pollutants by photocatalysis at surfaces of the filter cover (24).

12. The healthcare cum optimal illumination device according to claim 1, wherein the light source (26) includes different electric light sources capable of emitting light in different colors and brightness.

* * * * *